US007150871B2

(12) United States Patent
Huang et al.

(10) Patent No.: US 7,150,871 B2
(45) Date of Patent: Dec. 19, 2006

(54) TREATMENT OF ACUTE LUNG INJURY, FIBROSIS AND METASTASIS WITH ANTAGONISTS OF αVβ6

(75) Inventors: Xiaozhu Huang, Daly City, CA (US); Dean Sheppard, Oakland, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 10/754,435

(22) Filed: Jan. 9, 2004

(65) Prior Publication Data
US 2004/0208878 A1 Oct. 21, 2004

Related U.S. Application Data (63) Continuation of application No. 09/818,416, filed on Mar. 27, 2001, now Pat. No. 6,692,741, which is a continuation of application No. 09/130,870, filed on Aug. 7, 1998, now abandoned.

(60) Provisional application No. 60/055,060, filed on Aug. 8, 1997.

(51) Int. Cl.
A61K 39/395 (2006.01)
(52) U.S. Cl. .................. 424/155.1; 424/143.1
(58) Field of Classification Search .............. 424/143.1, 424/155.1
See application file for complete search history.

(56) References Cited

U.S. PATENT DOCUMENTS

| 5,514,788 | A | 5/1996 | Bennett et al. | |
|---|---|---|---|---|
| 5,654,270 | A | 8/1997 | Ruoslahti et al. | |
| 5,962,643 | A | 10/1999 | Sheppard et al. | |
| 6,492,332 | B1* | 12/2002 | Demopulos et al. | .......... 514/12 |

FOREIGN PATENT DOCUMENTS

WO   WO 90/06767 A1   6/1990

OTHER PUBLICATIONS

B.A. Imhof et al. Current Top Microbiol Immunol. 1996; 213 (Pt1): 195-203.*
A Weinacker et al. J Biol Chem, 1994; 269(9): 6940-6948.*
G Dermer. Biotechnology 12, Mar. 1994.*
M Osband et al. Immunol Today 11(6): 193-195, 1990.*
E Harlow et al. Antibodies Cold Spring Harbor, 1988.*
R Fenton et al. J NCI 87(4), 1995.*
A. Mountain. TibTech 18: 119127, 2000.*
Marshall et al. Comparative analysis of integrins in vitro and in vivo in uveal and cutaneous melanomas. Br J Cancer. Feb. 1998;77(4):522-9.*
Weiner LM. An overview of monoclonal antibody therapy of cancer. Semin Oncol. Aug. 1999;26(4 Suppl 12):41-50.*
Breuss et al. Expression of the beta 6 integrin subunit in development, neoplasia and tissue repair suggests a role in epithelial remodeling. J Cell Sci. Jun. 1995;108 ( Pt 6):2241-51.*
Dillman RO.Monoclonal antibodies for treating cancer. Ann Intern Med. Oct. 1, 1989;111(7):592-603.*
Agrez, M., et al. "The αvβ6 Integrin Promotes Proliferation of Colon Carcinoma Cells through a Unique Region of the β6 Cytoplasmic Domain," *The Rockefeller University Pres.*, vol. 127, No. 2, pp. 547-556 (Oct. 1994).
Agrez, M., et al. "Integrin αvβ6 Enhances Coxsackievirus B1 Lytic Infection of Human Colon Cancer Cells," *Virology* 239, 71-77 (1997).
Berkow, R., M.D., et al. "The Merck Manual of Diagnosis and Therapy," *Merck Professional Handbooks* pp. 642-646 16th Editon, 1992.
Cheresh, et al., "A Novel Vitronectin Receptor Integrin (αvβx) Is Responsible for Distinct Adhesive Properties of Carcinoma Cells," *Cell*, vol. 57, 59-69 (Apr. 7, 1989).
Edgington, Stephen M., "How Sweet It Is: Selectin-Mediating Drugs," *Biotechnology*, 10:383-389 (1992).
Griffiths, M., et al., "Inactivation of the β6 Integrin Subunit Gene Protects Against Bleomycin-Induced Pulmonary Fibrosis," Molecular Biology of the Cell, Bethesda, MD vol. 7, p. 166A (1996).
Freed, E. et al., "A novel integrin β subunit is associated with the vitronectin receptor α subunit ($α_v$) in a human osteosarcoma cell line and is a substrate for protein kinase C," *The EMBO Journal*, vol. 8, No. 10, pp. 2955-2965 (1989).
Holzmann, B., et al., "Identification of a Murine Peyer's Patch-Specific Lymphocyte Homing Receptor as an Integrin Molecule with an α Chain Homologous to Human VLA-4α," *Cell*, 56:37-46 (Jan. 13, 1989).
Huang, X., et al., "Inactivation of the Integrin β6 Subunit Gene Reveals a Role of Epithelial Integrins in Regulating Inflammation in the Lungs and Skin," *The Journal of Cell Biology*, 133:4, Plaintiff. 921-928 (May 1996).
Huang, X., et al., "Expression of the Human Integrin β6 Subunit in Alveolar Type II Cells and Bronchiolar Epithelial Cells Reverses Lung Inflammation in β6 Knockout Mice," *Am. J. Respir. Cell Mol.. Biol.*, 19:636-642 (1998).
Hynes, R.O., et al., "Contact and Adhesive Specificities in the Associations, Migrations, and Targeting of Cells and Axons," *Cell*, 68:303-322 (1992).
Kajiji et al., "A novel integrin ($α_Eβ_4$) from human epithelial cells suggests a fourth family of integrin adhesion receptors," *The EMBO Journal*, 8:673-680 (1989).

(Continued)

Primary Examiner—Maher M. Haddad
(74) Attorney, Agent, or Firm—Townsend and Townsend and Crew LLP (57) ABSTRACT Methods and compositions comprising antagonists of αvβ6 are provided for the treatment of acute lung injury fibrosis.

5 Claims, 3 Drawing Sheets

OTHER PUBLICATIONS

Kogan et al., "A Single Amino Acid Residue Can Determine the Ligand Specificity of E-selectin," *The Journal of Biological Chemistry*, vol. 270 No. 23 :14047-14055 (1995).

Ngo et al., "Computational Complexity, Protein Structure Prediction, and the Levinthal Paradox," *The Protein Folding Problem and Tertiary Structure Prediction*, K. Merz, Jr. and S. LeGrand, Editors, Birkhauser Boston 1994 pp. 491-495.

Ramaswamy et al., "Cloning, primary structure and properties of a novel human integrin β subunit," *The EMBO Journal*, vol. 9, No. 5 pp. 1561-1568 (1990).

Rozdzinski et al., "Antiinflammatory Effects in Experimental Meningitis of Prokaryotic Peptides that Mimic Selectins," *The Journal of Infectious Diseases*, 168:1422-8 (1993).

Ruoslahti et al., "New Perspectives in Cell Adhesion: RGD and Integrins," *Science* vol. 238 pp. 491-497 (Oct. 23, 1987).

Sheppard et al., "Complete Amino Acid Sequence of a Novel Integrin β Subunit ($β_6$) Identified in Epithelial Cells Using the Polymerase Chain Reaction," *The Journal of Biological Chemistry*, vol. 265 No. 20 pp. 11502-11507 (1990).

Sheppard et al., "Use of Homology PCR To Identify A Novel Integrin Beta Chain From Airway Epithelium," *Am Rev. Respir. Dis*, 141:A707 (1990).

Ward et al., "Blocking of adhesion molecules in vivo as antiflammatory therapy," *Therapeutic Immunology*, 1:165-171 (1994).

Weinacker et al., "Role of the Integrin αvβ6 in Cell Attachment to Fibronectin," *The Journal of Biological Chemistry*, vol. 269 No. 9 pp. 6940-6948 (1994).

Yokosaki et al., "Differential Effects of the Integrins α9β1, αvβ3, and αvβ6 on Cell Proliferative Responses to Tenascin," *The Journal of Biological Chemistry*, vol. 271 No. 39 pp. 24144-24150 (1996).

Vaderslice, et al., "A Cyclic Hexapeptide is a Potent Antagonist of $α_4$ Integrins"; *The Journal of Immunology* 158: 1710-1718 (1997).

JPA van Pelt, et al., "The Regulation of CD11b Integrin Levels on Human Blood Leukocytes and Leukotriene B4-Stimulated Skin by a Specific Leukotriene B4 Receptor Antagonist (LY293111)"; *Biochemical Pharmacology* vol. 53, pp. 1005-1012 (1997).

McIntyre, et al., "Regulation of Human T Lymphocyte Coactivation with an $α_4$ Integrin Anatagonist Peptide"; *The Journal of Immunology* 158: 4180-4186 (1997).

Engleman, et al., "A Peptidomimetic Antagonist of the $α_v β_3$ Integrin Inhibits Bone Resorption In Vitro and Prevents Osteoporosis In Vivo"; *J. Clin. Invest.*, vol. 99, No. 9 (May 1997).

Kapil, et al., "Biological Matrix-Dependent Pharmacokinetic and Pharmacodynamic Parameters of a Novel Platelet Glycoprotein IIB/IIIA Receptor Antagonist, XU063, In Beagle Dogs"; *Thrombosis Research*, vol. 86, No. 3, pp. 221-232 (1997).

Craig, et al., "Concept and Progress in the Development of RGD-Containing Peptide Pharmaceuticals"; *Biopolymers (Peptide Science)*, vol. 37, 157-175 (1995).

"The Merck Manual of Diagnosis and Therapy"; *Merck Professional Handbooks*, Sixteenth Edition (1992) pp. 642-646.

Breuss, J. M. et al., "Expression of the β6 Integrin Subunit in Development, Neoplasia and Tissue Repair Suggests a Role in Epithelial Remodeling"; *Journal of Cell Science*, 108:2241-2251 (1995).

Lehmann, M. et al., "A Monoclonal Antibody Inhibits Adhesion to Fibronectin and Vitronectin of a Colon Carcinoma Cell Line and Recognizes the Integrins"; *Cancer Research*, 54:2102-2107 (Apr. 15, 1994).

Wang, A. et al., "Differential Regulation of Airway Epithelial Integrins by Growth Factors"; *Am. J. Respir. Cell Mol. Biol.*, vol. 15:664-672 (1996).

Suzuki, Shintaro et al.; "Amino Acid Sequence of the Vitronectin Receptor α Subunit and Comparative Expression of Adhesion Receptor mRNAs"; 1987, *The Journal of Biological Chemistry*, vol. 262, No. 29, pp. 14080-14085.

* cited by examiner

TREATMENT OF ACUTE LUNG INJURY, FIBROSIS AND METASTASIS WITH ANTAGONISTS OF αVβ6

This application is a continuation of U.S. patent application Ser. No. 09/818,416, filed Mar. 27, 2001 now U.S. Pat. No. 6,692,741, which is a continuation of U.S. patent application Ser. No. 09/130,870, filed Aug. 7, 1998, now abandoned, which application claims priority to U.S. Provisional Application No. 60/055,060, filed Aug. 8, 1997, each of which are incorporated by reference in their entirety.

This work was supported in part by HIH grant numbers HL47412 and HL53949. The U.S. government may have certain rights in this invention.

BACKGROUND OF THE INVENTION

Integrins are heterodimeric cell adhesion receptors composed of two subunits, α and β. The integrin αvβ6 is a fibronectin and tenascin receptor expressed predominantly by epithelial cells. In healthy adult primate tissues, β6 mRNA and protein are rarely detected, although β6 is expressed during fetal development, wound healing, and in some epithelial tumors. When the β6 subunit is expressed in a colon carcinoma cell line, from which it is normally absent, expression of the subunit confers an enhanced ability to proliferate. An 11 amino acid COOH-terminal region, unique to the β6 subunit, is required for the proliferation-enhancing activity of the αvβ6 integrin (Agrez et al. *J. Cell. Biol.* 127:547–556 (1994). β6 expression is induced in type II aveolar epithelial cells during injury caused by injection of live bacteria, and β6 expression is observed at focal sites of subclinical inflammation, as well as in a variety of clinical specimens from patients with chronic or acute inflammation of the lungs or kidneys (Breuss et al. *J. Cell Sci.* 108: 2241–2251 (1995).

Huang et al. (*J. Cell Biol.* 133:921–928 (1996)) disclosed mice homozygous for a null mutation in the gene encoding the β6 subunit had juvenile baldness associated with infiltration of macrophages into the skin, and accumulated activated lymphocytes around conducting airways in the lungs.

Pulmonary fibrosis is a common disorder thought to be due to the destructive effects of products released from leukocytes (see, for example, Marshall et al., *Int. J. Biochem. Cell Bio.* 29:107–120 (1997)). Bleomycin-induced lung injury and pulmonary fibrosis are associated with and may depend upon the recruitment and activation of lymphocytes (Schrier, D. J. et al, *Am. J. Pathol.* 116:270–278 (1984)). Among proposed therapies for parenchymal lung injury and pulmonary fibrosis is the use of "anticytokine" therapeutic approaches (Coker et al. *Thorax* 52 (2): 294–296 (1997)).

However, current therapies for acute lung injury and pulmonary fibrosis are largely inadequate (see, for example, King et al., "Idiopathyic Pulmonary Fibrosis and other Interstitial Lung Diseases of Unknown Etiology," in *Textbook of Respiratory Medicine*, Murray and Nadel, eds., W. B. Saunders, Philadelphia, Pa., pp. 1827–1839 (1994)). Thus, a need exists for therapies for acute lung injury and pulmonary fibrosis. This need and others are addressed by the instant invention.

SUMMARY OF THE INVENTION

One aspect of the invention is a method of treating acute lung injury in a patient comprising administering to the patient a therapeutic dose of an antagonist of αvβ6. The invention also provides methods of inhibiting lung metastasis comprising administering to the patient a therapeutic dose of an antagonist of αvβ6. A further aspect of the invention is a method of treating fibrosis in a patient comprising administering to the patient a therapeutic dose of an antagonist of αvβ6.

A further aspect of the invention is a monoclonal antibody produced by the hybridoma ATCC HB12382.

A further aspect of the invention is the hybridoma ATCC HB12382.

DETAILED DESCRIPTION OF THE INVENTION

The instant invention provides methods and compositions for treatment of acute lung injury, such as but not limited to lung injury resulting from bacterial sepsis, hemorrhagic shock, toxic inhalation, and bleomycin and other drug-induced lung injury. Additionally, the compositions of the invention are useful in the treatment of fibrosis in epithelial organs, such as lung, liver, kidney, bladder, and esophagus.

Such compositions can be provided prophylactically or therapeutically to patients having or at risk of having symptoms of acute lung injury or fibrosis. For example, patients having had exposure to a toxic inhalant would likely be treated after such exposure, whereas a patient receiving bleomycin can be treated prophylactically and/or therapeutically. Typically, the compositions of the invention are administered on a daily basis for at least a period of 1–5 days, although patients with established pulmonary fibrosis, a progressive disease, may receive therapeutic doses for periods of months to years. As used herein, "therapeutic dose" is a dose which prevents, alleviates, abates, or otherwise reduces the severity of symptoms in a patient.

In some embodiments of the invention, antagonists of αvβ6 are provided. Such antagonists include but are not limited to antibodies which specifically bind to β6; antibodies which specifically bind to a αvβ6 ligand; ligands for αvβ6; antisense nucleic acids; and peptide; non-peptide, and peptidomimetic analogs of such ligands.

Antibodies can be synthetic, monoclonal, or polyclonal and can be made by techniques well known in the art. In a preferred embodiment, the antagonist is an antibody which specifically recognizes the cytoplasmic region of the β6 subunit (for example, see Weinacker et al. *J. Cell Bio.* 269:1–9 (1994)). For therapeutic applications, "human" monoclonal antibodies having human constant and variable regions are often preferred so as to minimize the immune response of a patient against the antibody. Such antibodies can be generated by immunizing transgenic animals which contain human immunoglobulin genes. See Jakobovits et al. *Ann NY Acad Sci* 764:525–535 (1995). In connection with synthetic and semi-synthetic antibodies, such terms are intended to cover but are not limited to antibody fragments, isotype switched antibodies, humanized antibodies (e.g., mouse-human, human-mouse, and the like), hybrids, antibodies having plural specificities, fully synthetic antibody-like molecules, and the like.

As discussed below, antibodies can be screened for the ability to block the binding of a ligand to the αvβ6 and/or for other properties, such as the ability to protect in vivo against bleomycin-induced pulmonary fibrosis. An exemplary antibody is 10D5 (ATCC deposit no. HB12382, deposited Aug. 6, 1997, American type Culture Collection, P.O. Box 1549, Manassas, Va. 20108).

In other embodiments of the invention, antagonists are used which are peptides, polypeptides, proteins, or peptido-mimetics designed as ligands for αvβ6 on the basis of the presence of the cell adhesion domain arginine-glycine-aspartic acid (RGD). The design of such molecules as ligands for the integrins is exemplified, for example, in Pierschbacher et al., *J. Cell. Biochem.* 56:150–154 (1994)); Ruoslahti, *Ann. Rev. Cell. Dev. Biol.* 12:697–715 (1996); Chorev et al. *Biopolymers* 37:367–375 (1995)); Pasqualini et al., *J. Cell. Biol.* 130:1189–1196 (1995)); and Smith et al., *J. Biol. Chem.* 269:32788–32795 (1994)).

In some embodiments of the invention, antisense nucleic acid molecules are used as antagonists of αvβ6. Antisense nucleic acid molecules are complementary oligonucleotide strands of nucleic acids designed to bind to a specific sequence of nucleotides to inhibit production of a targeted protein. The nucleotide sequence of the β6 integrin subunit was disclosed in U.S. Ser. No. 07/728,215, filed Jul. 11, 1991, hereby incorporated by reference in its entirety. These agents may be used alone or in combination with other antagonists. The antisense antagonist may be provided as an antisense oligonucleotide such as RNA (see, for example, Murayama et al. *Antisense Nucleic Acid Drug Dev.* 7:109–114 (1997)). Antisense genes may also be provided in a viral vector, such as, for example, in hepatitis B virus (see, for example, Ji et al., *J. Viral Hepat* 4:167–173 (1997)); in adeno-associated virus (see, for example, Xiao et al. *Brain Res.* 756:76–83 (1997)); or in other systems including but not limited to an HVJ(Sendai virus)-liposome gene delivery system ( see, for example, Kaneda et al. *Ann. N.Y. Acad. Sci.* 811:299–308 (1997)); a "peptide vector" (see, for example, Vidal et al. CR Acad. Sci III 32):279–287 (1997)); as a gene in an episomal or plasmid vector (see, for example, Cooper et al. *Proc. Natl. Acad. Sci. U.S.A.* 94:6450–6455 (1997), Yew et al. *Hum Gene Ther.* 8:575–584 (1997)); as a gene in a peptide-DNA aggregate (see, for example, Niidome et al. *J. Biol. Chem.* 272:15307–15312 (1997)); as "naked DNA" (see, for example, U.S. Pat. No. 5,580,859 and U.S. Pat. No. 5,589,466); and in lipidic vector systems (see, for example, Lee et al. *Crit Rev Ther Drug Carrier Syst.* 14:173–206 (1997))

Candidate antagonists of αvβ6 can be screened for function by a variety of techniques known in the art and/or disclosed within the instant application, such as protection against bleomycin-induced fibrosis in a mouse model; inhibition of the proliferation of tumor cells (Agrez et al., *J. Cell Bio.*, 127:547–556 (1994)); and inhibition of cell migration and/or inhibition of cell adhesion (see Experimental Examples section).

A multitude of appropriate formulations of the antagonists of the invention can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, in *Goodman and Gilman's the Pharmacological Basis of Therapeutics*, 7th Edition (1985), MacMillan Publishing Company, New York, and *Remington's Pharmaceutical Sciences* 18th Edition, (1990) Mack Publishing Co, Easton Pa. Methods for administration are discussed therein, including oral, intravenous, intraperitoneal, intramuscular, transdermal, nasal, iontophoretic administration, and the like.

The compositions of the invention may be administered in a variety of unit dosage forms depending on the method of administration. For example unit dosage forms suitable for oral administration include solid dosage forms such as powder, tablets, pills, capsules, and dragees, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such as antibody, or with other therapeutic or immunogenic compositions. Thus, liposomes either filled or decorated with a desired composition of the invention of the invention can delivered systemically, or can be directed to a tissue of interest, where the liposomes then deliver the selected therapeutic/immunogenic peptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. *Ann. Rev. Biophys. Bioeng.* 9:467 (1980), U.S. Pat. Nos. 4,235,871, 4,501,728, 4,837,028, and 5,019,369, incorporated herein by reference.

A liposome suspension containing a composition of the invention may be administered intravenously, locally, topically, etc. in a dose which varies according to, inter alia, the manner of administration, the composition of the invention being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more compositions of the invention of the invention, and more preferably at a concentration of 25%–75%.

For aerosol administration, the compositions of the invention are preferably supplied in finely divided form along with a surfactant and propellant. Typical percentages of compositions of the invention are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

The constructs of the invention can additionally be delivered in a depot-type system, an encapsulated form, or an implant by techniques well-known in the art. Similarly, the constructs can be delivered via a pump to a tissue of interest.

Any of the foregoing formulations may be appropriate in treatments and therapies in accordance with the present invention, provided that the active agent in the formulation is not inactivated by the formulation and the formulation is physiologically compatible.

The following examples are provided to illustrate certain aspects of the present invention and not intended as limiting the subject matter thereof.

EXPERIMENTAL EXAMPLES

I. Introduction

Pulmonary fibrosis is a common disorder thought to be due to the destructive effects of products released from leukocytes. Although the respiratory epithelium is damaged during the development of fibrosis, epithelial cells themselves have not been previously shown to contribute to this process. We examined the effects of bleomycin, a drug known to cause pulmonary fibrosis, on mice expressing a null mutation of a single integrin subunit (β6) gene that is completely restricted to epithelial cells. β6−/− mice were dramatically protected from bleomycin-induced fibrosis. Therapies targeting this integrin could therefore provide new approaches for treatment of this largely untreatable disorder.

The integrin αvβ6 is expressed exclusively on epithelial cells, principally during organogenesis and in response to injury. β6−/− mice have exaggerated inflammatory responses to cutaneous and airway injury, but develop and reproduce normally (Huang, X. Z. et al., *J. Cell Biol.* 133:921–928 (1996)).

Figure 1:
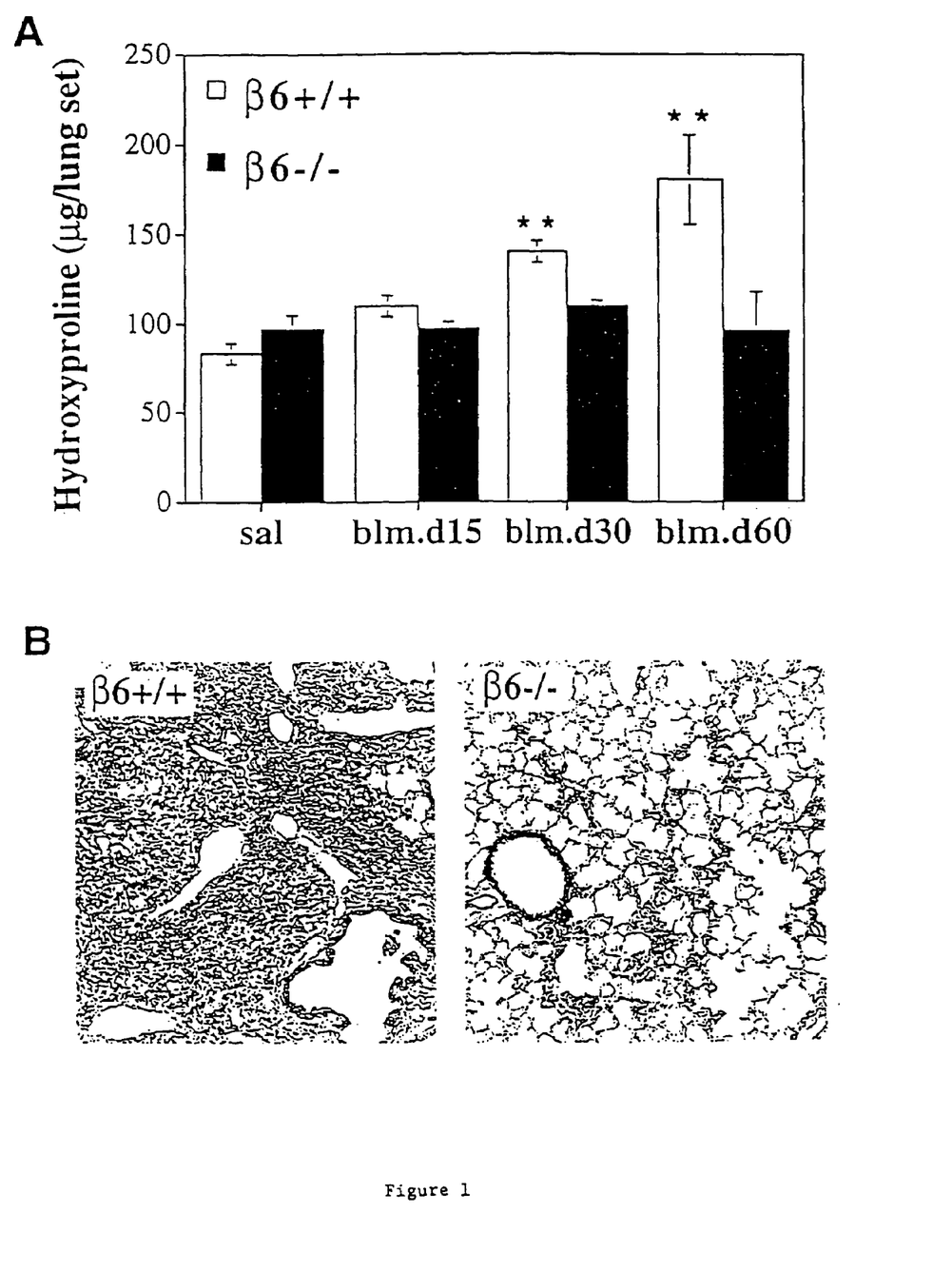
FIG. 1A is a graph comparing lung hydroxyproline content in mice expressing a null mutation of the β6 integrin subunit gene with control mice in the presence of bleomycin (blm) or saline (sal).
FIG. 1B is a photograph of trichrome staining of low power lung sections demonstrating dense accumulation of collagenous extracellular matrix in lungs of bleomycin treated wild type (β6+/+) but not β6−/− mice 30 days after treatment.

II. Inactivation of the β6 Integrin Subunit Gene Protects Mice Against Bleomycin-induced Pulmonary Fibrosis The pulmonary toxicity of bleomycin (0.03 units (u) in 60 μl saline) or saline vehicle (60 μl) given by intratracheal injection was examined in age and sex matched wild type (β6+/+) and β6−/− mice of the 129SVEMS/ter strain. Pulmonary fibrosis was evaluated at 15, 30 and 60 days after treatment by examination of lung morphology and by measurement of hydroxyproline content, an index of collagen deposition. Fibrosis was significant in bleomycin-treated wild type mice by 30 days and progressed to 60 days (FIGS. 1A–1B). By contrast, in β6−/− mice lung morphology remained nearly normal throughout the experiment, with only small patches of fibrosis; and the lung hydroxyproline content was not significantly different from that measured in saline-treated animals at any time point. This finding was not unique to pure 129 mice, since similar results were obtained in offspring of 129 by C57B1/6 intercrosses. These unexpected results indicated that expression of the integrin αvβ6 is required for the induction of pulmonary fibrosis.

Figure 2:
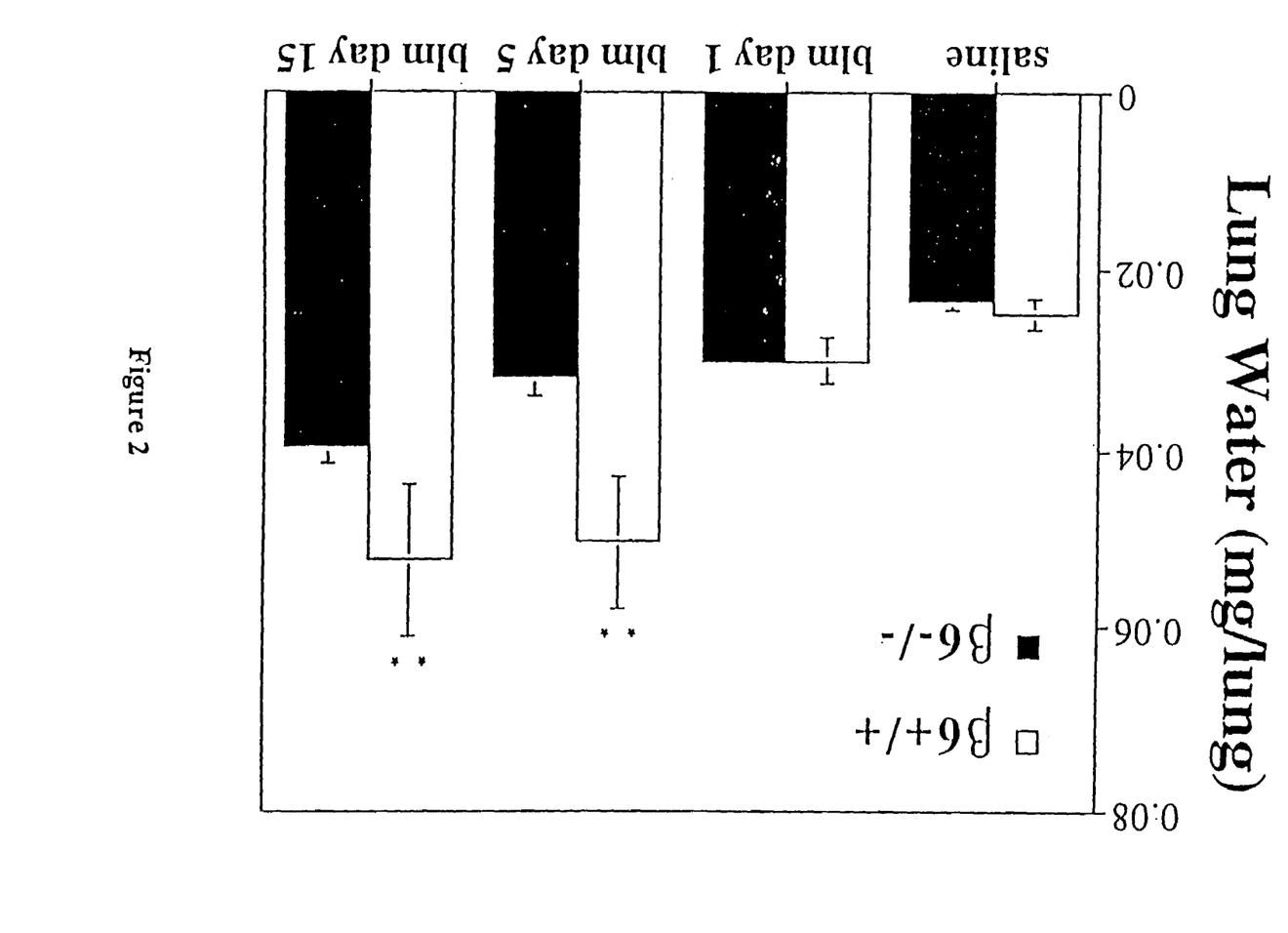
FIG. 2 is a graph comparing the increase in lung water in wild type mice (β6+/+) compared to β6−/− mice in the presence of bleomycin (blm) or saline (sal).

To determine the role of αvβ6 in the early stages of bleomycin-induced fibrosis, we measured lung water content, a marker of pulmonary edema resulting from increased vascular permeability, at 1, 5 and 15 days after administration of bleomycin or saline. In wild type mice, lung water was increased maximally by 5 days and remained increased for up to 15 days after bleomycin (FIG. 2). As with pulmonary fibrosis, β6−/− mice were largely protected from this early effect of bleomycin, indicating a role for epithelial αvβ6 prior to the development of bleomycin-induced vascular leakage.

Figure 3:
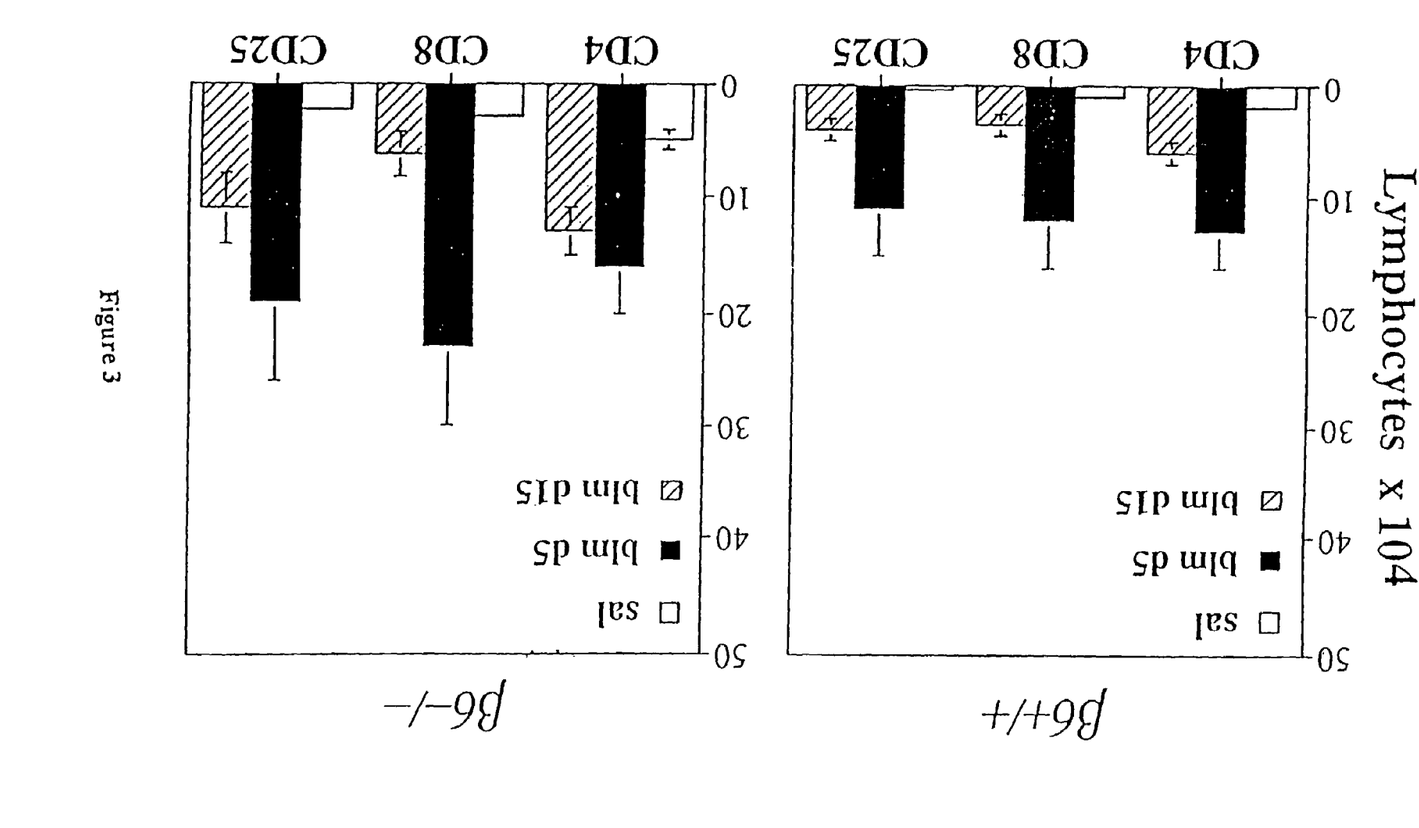
FIG. 3 is a graph comparing the recruitment of lymphocytes in wild type (β6+/+) and β6−/− mice after administration of bleomycin (blm) or saline (sal).

We have previously reported that β6−/− mice demonstrate exaggerated mononuclear cell inflammatory responses in the skin and airways (Huang, X. Z. et al., *J. Cell. Biol.* 133: 921–928 (1996)). Bleomycin-induced lung injury and pulmonary fibrosis are associated with and may depend upon the recruitment and activation of lymphocytes (Schrier, D. J. et al., *Am. J. Pathol.* 116:270–278 (1984)). In order to determine whether the resistance of β6−/− mice to bleomycin-induced injury and fibrosis was due to altered lymphocyte recruitment or activation, we counted CD4+ and CD8+ lymphocytes and evaluated lymphocyte activation by measuring expression of the interleukin 2-receptor (CD25) in cells obtained from minced lungs of saline or bleomycin-treated mice at 5 and 15 days after treatment. Consistent with our earlier report, there were more CD4+, CD8+ and CD25+ cells in the lungs of β6−/− mice than in wild type animals. Bleomycin induced a large increase in the numbers of CD4 and CD8 expressing lymphocytes, and marked increase in the percentage of lymphocytes expressing CD25 (FIG. 3), in both wild type and β6−/− mice. In both wild type and β6−/− mice recruitment and activation of lung lymphocytes was maximal 5 days after bleomycin administration and had begun to decline by 15 days. Without being limited to any one theory, these data suggest that a failure of lymphocyte recruitment or activation in β6−/− mice is unlikely to underlie their protection from the damaging pulmonary effects of bleomycin.

The interaction of integrins with their matrix ligands modulates several important cell functions including proliferation (Agrez, M. et al., *J. Cell Biol.* 127:547–556 (1994)), survival (Lukacs, N. W. et al., *Eur. J. Immmunol.* 25:245–251 (1995)) and expression of cytokines (Miyake, S. et al., *J. Exp. Med.* 177:863–868 (1993)) and metalloproteinases (Werb, Z. et al., *J. Cell. Biol.* 109:877–889 (1989)). The β6 subunit has only been reported to form a single integrin heterodimer, αvβ6 and is restricted to epithelial cells. In parallel with the rapid induction of αvβ6 expression following epithelial injury, the local concentrations of at least two ligands for this integrin (fibronectin and tenascin) increase. We have previously reported that expression of αvβ6 plays a role in terminating mononuclear cell inflammatory responses in the skin and conducting airways of the lung (Huang X. Z. et al., *J. Cell. Biol.* 133:921–928 (1996)). The results reported here indicated that this integrin also plays a critical role in inducing lung injury and pulmonary fibrosis in response to bleomycin.

Respiratory epithelial cells have long been thought of principally as components of a passive barrier, separating other lung cells from the potentially toxic components of inhaled air. At this interface, however, these cells are well positioned to initiate and modulate local responses to injury. Recent evidence suggests that respiratory epithelial cells have the capacity to synthesize and secrete a number of proteins that can initiate and modulate responses to injury, including chemokines (e.g. interleukin-8, GROα. GROγ, RANTES, GMCSF, MIP-1α, and MCP-1), other cytokines (e.g., IL-6, IL-11, and IL15) and growth factors (e.g. TGFβ). Without being limited to any one theory, one possible mechanism by which epithelial αvβ6 could contribute to the development of lung injury and pulmonary fibrosis is by modulating expression of one or more of these proteins.

Current therapies of pulmonary fibrosis are largely inadequate. The results of the present study indicate that respiratory epithelial cells, and the epithelial integrin, αvβ6, play important roles in the pathogenesis of parenchymal lung injury and pulmonary fibrosis, and that therapies specifically designed to interfere with the function of this integrin are useful in the treatment of these largely untreatable lung diseases.

III. Generation of a Blocking Antibody

A. Generation of Monoclonal Antibody

To generate antibodies against αvβ6, β6−/− mice were immunized with either keratinocytes obtained from wild type mice or with recombinant secreted human αvβ6 (Weinacker et al., *J. Biol. Chem.* 269:6940–6948 (1994)) in Freund's adjuvant. Mouse splenocytes were harvested and fused with SP2/0 mouse myenoma cells according to standard procedures. β6-and mock-transfected SW 480 cells were used for screening the resulting supernatant by flow cytometry. Antibodies found to recognize β6-transfected but not mock transfected SW480 cells were used for later experiments.

B. Characterization of Monoclonal Antibodies

To generate antibodies against murine αvβ6, secreted human αvβ6 and murine keratinocytes were used as immunogens in 129/C57 background β6−/− mice. Supernatants from the hybridomas generated were screened for differential staining o mock-and β6-transfected SW480 cells. The resulting antibodies CSβ6 and 10D5 stained both human β6 expressed on SW480 cells and mouse β6 on wild type keratinocytes. CSβ6 was further characterized by immunoprecipitation of ($^{35}$S)-labeled murine keratinocyte lysate. This antibody precipitated heterodimers of the appropriate molecular mass to be αvβ6 from β6+/+ keratinocytes but not from β6−/− keratinocytes, indicating that these antibodies are specific for the integrin αvβ6.

We also tested both Csβ6 and 10D5 for blocking activity by performing cell adhesion assays with β6-transfected SW480 cells and murine keratinocytes on fibronectin. However, only 10D5 showed blocking activity on murine cells. 10D5 inhibited migration of wild type keratinocytes on fibronectin, to an identical degree to that seen in β6−/− keratinocytes.

C. Cell Adhesion Assay 96-well non-tissue culture treated polystyrene multiwell microtiter plates (Linbro/Titertek, Flow Laboratories, McLean, Va.) were coated with vitronectin, fibronectin or collagen. A 100 μl solution containing various amounts of matrix was added to the wells and incubated at 37° C. for 1 hour. After incubation, wells were washed with PBS, then blocked with 1% BSA in serum-free DMEM at 37° C. for 30 minutes. Control wells were filled with 1% BSA in DMBM. Cells were harvested in the same was as for the migration assay and resuspended in serum-free KGM, and then added to each protein-coated well in the presence or absence of PMA. For blocking experiments, cells were incubated with antibodies for 5 minutes at 4° C. before plating. The plates were centrifuged (top side up) at 10×g for 5 minutes before incubation for 1 hour at 34° C. in humidified 7% $CO_2$. Non-adherent cells were removed by centrifugation top side down at 48×g for 5 minutes. The attached cells were fixed with 1% formaldehyde and stained with 0.5% crystal violet, then the wells were washed with PBS. The relative number of cells in each well was evaluated by measuring the absorbance at 595 nm in a Microplate Reader (Bio-Rad).

D. Migration Assay

Cell migration assays were performed with matrix coated transwell plates (8 μm pores, Costar, Cambridge, Mass.). The undersurface of the membrane was coated with collagen (10 μg/ml), fibronectin (10 μg/ml) or vitronectin (10 μg/ml) in PBS for 1 hour at 37° C. and blocked with 1% BSA. Primary cultured keratinocytes were harvested with trypsin/EDTA and trypsin was inactivated with soybean trypsin inhibitor. Cells were suspended in serum-free KGM and plated in the upper chamber at a density of 3.6×10$^4$ per well in 100 μl medium in the presence or absence of phorbol myristate acetate (PMA, 10 ng/ml). For inhibition experiments, antibodies were added into upper and lower chambers in the presence of PMA. After a 6 hour incubation, cells were fixed with 2% paraformaldehyde and stained with 0.5% crystal violet in 1% formaldehyde. Cells in the upper chamber were removed and cells on the lower surface were counted with a 10×grid at high power magnification (40×). Multiple fields were counted and averaged for each condition studied.

IV. β6 Knockout Mice Have Reduced Incidence of Lung Metastases

A transgenic mouse line that spontaneously develops metastatic breast cancer (MMTV-mTAg mice) was crossbred with beta-6 knockout mice. Offspring mice that lacked β6 developed fast growing primary mammary tumors, but had greatly reduced incidence and extent of lung metastasis compared to littermates that expressed β6. Immunohistochemistry showed that β6 is strongly expressed around the edge of metastatic lesions. This suggests that β6 is required for maximal metastasis in this model.

Since β6 knockout mice have chronic lung inflammation, it is possible that reduced metastasis is due to the presence of inflammation in the lung interfering with metastatic growth. Two experiments were carried out to address this issue:

1. A β6 expressing cell line derived from the primary tumor was injected into syngeneic mice that were either wild-type or β6 knockout. Lung metastasis rapidly occurred in both groups of mice, suggesting that the presence of inflammation in the knockout mice does not interfere with tumor cell growth in the lung.
2. Cell lines derived from tumors of either beta-6 knockout or wild-type mice were injected into syngeneic wild-type mice. Wild-type cell lines invariably gave rise to lung tumors, while knockout cell lines did not. This experiment suggests that tumor cell β6 is required for maximal metastasis in this system.

All references (including books, articles, papers, patents, and patent applications) cited herein are hereby expressly incorporated by reference in their entirety for all purposes.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. A method of treating or reducing the incidence of a breast or lung metastatic cancer in a subject, wherein the metastatic cancer cells in the subject express integrin β6, the method comprising administering to the subject an effective dose of an antibody that specifically binds to a β6 subunit of αvβ6.

2. The method of claim 1, wherein the antibody is a monoclonal antibody.

3. The method of claim 1, wherein the antibody is 10D5 (ATCC deposit number HB12382).

4. The method of claim 1, wherein the cancer is breast cancer.

5. The method of claim 1, wherein the incidence of lung metastases are reduced.

\* \* \* \* \*

UNITED STATES PATENT AND TRADEMARK OFFICE
Certificate

Patent No. 7,150,871 B2                      Patented: December 19, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Xiaozhu Huang, Daly City, CA (US); Dean Sheppard, Oakland, CA (US); and Robert Pytela, San Francisco, CA (US).

Signed and Sealed this Fifteenth Day of April 2008.

*CHRISTINA CHAN*
*Supervisory Patent Examiner*
*Art Unit 1644*

UNITED STATES PATENT AND TRADEMARK OFFICE
Certificate

Patent No. 7,150,871 B2

Patented: December 19, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Xiaozhu Huang, Daly City, CA (US); Dean Sheppard, Oakland, CA (US); and Robert Pytela, San Francisco, CA (US).

Signed and Sealed this Twentieth Day of May 2008.

EILEEN B. O'HARA
*Supervisory Patent Examiner*
Art Unit 1644